US006419907B1

(12) United States Patent
Hocquaux et al.

(10) Patent No.: US 6,419,907 B1
(45) Date of Patent: Jul. 16, 2002

(54) USE OF CUPRIC COMPLEX OF 3,5-DISOPROPYLSALICYLIC ACID BY WAY OF A COSMETIC PRODUCT AND COSMETIC COMPOSITIONS CONTAINING THIS COMPOUND FOR PROTECTING THE HUMAN EPIDERMIS AGAINST UV RADIATION

(75) Inventors: Michel Hocquaux, Paris; Georges Rosenbaum, Asnières, both of (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 07/180,556

(22) Filed: Apr. 12, 1988

(30) Foreign Application Priority Data

Apr. 13, 1987 (LU) ................................................ 86844

(51) Int. Cl.$^7$ ............................ A61K 7/42; A61K 7/44; A61K 7/00

(52) U.S. Cl. ......................... 424/59; 424/60; 424/400; 424/401

(58) Field of Search ............................ 424/59, 60, 400, 424/401

(56) References Cited

U.S. PATENT DOCUMENTS

| 2,041,874 A | | 5/1936 | Stockelbach | |
| 2,695,858 A | | 11/1954 | Lisle, Jr. | |
| 2,974,089 A | | 3/1961 | Alexander | |
| 3,100,717 A | | 8/1963 | Long | |
| 3,317,382 A | | 5/1967 | Brunner | |
| 3,821,370 A | | 6/1974 | Tenta | 424/145 |
| 3,884,949 A | * | 5/1975 | Eicke et al. | 556/115 |
| 3,949,072 A | | 4/1976 | Tenta | 424/145.1 |
| 4,136,165 A | | 1/1979 | Muller et al. | 424/60 |
| 4,154,823 A | | 5/1979 | Schutt | 424/195.1 |
| 4,199,576 A | | 4/1980 | Reller | 424/230.1 |
| 4,221,785 A | | 9/1980 | Sorenson | 424/230 |
| 4,248,861 A | | 2/1981 | Schutt | 424/60 |
| 4,264,581 A | | 4/1981 | Kerkhof | 424/60 |
| 4,287,190 A | | 9/1981 | Boettcher et al. | 424/230.1 |
| 4,514,383 A | | 4/1985 | Murray | 424/59 |
| 4,522,807 A | | 6/1985 | Kaplan | 424/59 |
| 4,559,225 A | | 12/1985 | Fourman | 424/59 |
| 4,597,963 A | | 7/1986 | Deckner | 424/59 |
| 4,603,046 A | | 7/1986 | Georgalas | 424/59 |
| 4,613,499 A | | 9/1986 | Conner | 424/59 |
| 4,657,928 A | * | 4/1987 | Sorenson | 514/499 |
| 4,663,155 A | | 5/1987 | Murray | 424/59 |
| 4,699,779 A | | 10/1987 | Palinczar | 424/59 |

FOREIGN PATENT DOCUMENTS

| EP | 0077742 | * | 4/1973 | | 424/60 |
| EP | 0 321 929 | | 12/1987 | | |
| EP | 0 293 579 | | 12/1988 | | |
| WO | WO84/04922 | | 12/1984 | | |
| WO | WO8404922 | | 12/1984 | | 424/230 |

OTHER PUBLICATIONS

Chem. Abs., 1988, vol. 108, pp. 182872q, Mohammed.*
Chemical Abstracts, vol. 105,1986, p. 378.
D. H. Liem and L. T. H. Hilderink, "U. V. Absorbers in Sun Cosmetics 1978," *International Journal of Cosmetic Science*, 1979.
John R. J. Sorenson, "Copper Chelates as Possible Active Forms of the Antiarthritic Agents," *Journal of Medicinal Chemistry*, 1976, vol. 19, No. 1, pp. 135–148.
Miyachi et al, "Decreased Skin Superoxide Dismutase Activity", Journal of Investigative Dermatology, 1987, pp. 111–112 Sagarin, Cosmetics Science and Technology, 1957, pp. 189–205.
Merck Index, Merck & Co., Inc. 1989, excerpts from THER–15,16 and 24, pp. 134, 749, 964, 980, 981, 1156, 1254, 1324, 1511.
Danno, K. et al, "Sunburn Cell: Factors Involved In Its Formation", Photochemistry and Photobiology, vol. 45, No. 5, 1987, pp. 683–690.
Greenway, F., "Mononuclear and Binuclear Copper (II) Complexes of 3, 5–Diisopropylsalicylic Acid", Inorganica Chimica Acta, 145 (1988) , pp. 279–284.
Encyclopedia of UV Absorbers for Sunscreen Products, Cosmetics and Toiletries, vol. 102, Mar. 1987, pp. 21–39.
Al–Haji, G. et al, 1 "Effect of Ultraviolet Light on the Skin", The West Virginia Medical Journal, Dec. 1973, vol. 69, No. 12, pp. 351–352.
Steadman's Medical Dictionary, 24$^{th}$ Ed., Williams & Wilkins, pp. 484–485.
Oxy Radicals and Their Scavenger Systems, vol. II Cellular and Medical Aspects, Elsevier Biomedical, 1983, pp. 173–178, 208, 209.
Leuthauser, S. et al, "Antitumor Effect of a Copper Coordination Compound with Superoxide Dismutase–Like Activity", JNCL, vol. 66, No. 6, Jun. 1981, pp. 1077–1081.
Harrison's Principles of Internal Medicine, Tenth Edition, McGraw–Hill, pp. 275–276.
Miyachi, Y. et al, "Sunburn cell formation is prevented by Scavenging oxygen intermediates", Clinical and Experimental Dermatology (1983) , 8, pp. 305–310.
Kensler, T. et al, "Roll of Oxygen Radicals in Tumor Promotion", Environmental Mutagenesis (1984) , 6, pp. 593–616.
Roschchupkin, D. et al, "Inhibition of Ultraviolet Light–Induced Erythema by Antioxidants", Dermatol. Res. (1979) 266, pp. 91–94.

(List continued on next page.)

*Primary Examiner*—Jose G. Dees
(74) *Attorney, Agent, or Firm*—Jacobson Holman PLLC

(57) ABSTRACT

The invention relates to a cosmetic composition for protecting the skin against ultraviolet radiation of wavelengths between 280 and 400 nm, comprising, in a cosmetic vehicle containing at least one fatty phase, an effective amount of copper (II) bis(3,5-diisopropylsalicylate).

The composition can contain, in addition, one or more UV-B and/or UV/A sunscreens.

10 Claims, No Drawings-

OTHER PUBLICATIONS

Allen, N.S. et al, "Synthesis and thermal and photooxidative behaviour of 1, n–bis (3–hydroxy–4–benzoylphenoxy) alkanes in polyolefin films", Polymer Degradation and Stability, 35, 1992 pp. 23.

Diamond, L., et al, "Tumor Promoters and the Mechanism of Tumor Promotion", Advances in Cancer Research, vol. 32, pp. 16–18.

Veret, G., "Les Filtres Solaires", Laboratories SVR, France, Dec. 1984.

Sorenson, J., "Copper Chelates as Possible Active Forms of the Antiarthritic Agents", Journal of Medicinal Chemistry, 1976, vol. 19, No. 1, pp. 135–148.

Chemical Abstracts, vol. 105, 1986, p. 378.

* cited by examiner

USE OF CUPRIC COMPLEX OF 3,5-DIISOPROPYLSALICYLIC ACID BY WAY OF A COSMETIC PRODUCT AND COSMETIC COMPOSITIONS CONTAINING THIS COMPOUND FOR PROTECTING THE HUMAN EPIDERMIS AGAINST UV RADIATION

The present invention relates to the use of a cupric complex of 3,5-diisopropylsalicylic acid by way of a cosmetic product, to a cosmetic composition containing the said complex and to a process for protecting the human epidermis against ultraviolet radiation using the said cosmetic composition.

It is well-known that, when subjected to solar irradiation, the skin undergoes various modifications and, in particular, certain injuries.

Among the injuries caused to the skin by the sun, the most dramatic is unquestionably sunburn or solar erythema, which appears, depending on the intensity and duration of irradiation, between the second and the twenty fourth hour after exposure to the sun. Solar erythema may manifest itself by a slight pink coloration of the skin, but can also lead to genuine burns accompanied by considerable disorders of the general condition.

Solar radiation can also cause cellular modifications in the skin. The formation in the epidermis of keratinocytes that are degraded or even destroyed by UV radiation is observed in particular, these being degenerate cells which are necrosed through the action of solar radiation, generally known by the name of "sunburn cells".

The region of solar radiation responsible for these phenomena falls within the ultraviolet radiation, that is to say in the range of wavelengths between 280 and 400 nm. An effort has hence been made to protect the skin by applying substances possessing an absorption maximum in this region. These substances constitute what are known as sunscreens. Depending on the quantity of sunscreen applied on the skin, a larger or smaller portion of the damaging rays is stopped, thereby proportionately decreasing the appearance of the injuries caused to the skin.

Many sunscreens have already been recommended, having a diversity of chemical natures and possessing a variety of physicochemical properties, especially as regards solubility (water-soluble or fat-soluble products). These compounds provide what may be referred to as a primary protection.

However, the absorption of the ultraviolet radiation by the screens is never complete. There hence remains a residual amount of energy-rich radiation which reaches the skin. Thus, sunscreens lessen the injuries created in the skin without completely abolishing them.

It is hence desirable to combine the sunscreens with, or replace them by, products capable of decreasing the injuries caused to the skin by a phenomenon other than simple screening.

The Applicant has discovered that the application on the skin of a complex composed of two molecules of 3,5-diisopropylsalicylic acid and one atom of copper, namely copper (II) bis(3,5-diisopropylsalicylate), of formula

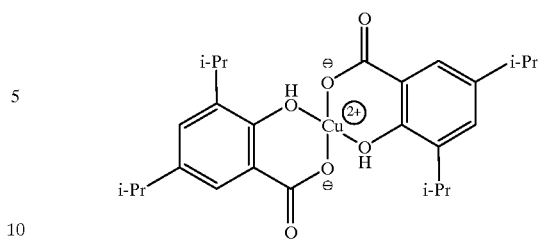

surprisingly enabled the intensity of the solar erythema and the number of degraded keratinocytes to be reduced, without these properties being due to a distinct absorbing power in the ultraviolet radiation region. These properties persist in the presence of sunscreens.

The cupric complex of 3,5-diisopropylsalicylic acid is a known compound whose synthesis is described in "Journal of Medicinal Chemistry", 1976, Vol. 19, No. 1, p. 135–148. This document, and also U.S. Pat. No. 4,221,785, also describe the anti-inflammatory and anti-ulcer properties of this cupric complex, which can be administered parenterally, especially subcutaneously, and orally. International Patent Application WO 84/04,922 describes this compound as an intramuscularly administered anti-tumour agent.

However, the topical application of this cupric complex in the cosmetics field, which forms the subject of the present invention, is not recommended in any of these documents of the prior art cited above. In point of fact, the Applicant has been able to demonstrate that the action of this cupric complex with respect to UV radiation is exerted chiefly at the skin surface.

The subject of the present invention is hence the use of copper (II) bis(3,5-diisopropylsalicylate) by way of a cosmetic product.

The subject of the present invention is also a cosmetic composition which is useful for protecting the skin against ultraviolet radiation of wavelengths between 280 and 400 nm comprising, in a cosmetically acceptable vehicle containing at least one fatty phase, an effective amount of copper (II) bis(3,5-diisopropylsalicylate).

Another subject of the invention consists of a cosmetic composition for protecting the skin comprising, in a cosmetically acceptable vehicle containing at least one fatty phase, the said cupric complex of 3,5-diisopropylsalicylic acid and at least one sunscreen which absorbs ultraviolet rays of wavelengths between 280 and 400 nm.

The present invention also relates to a process for protecting the skin against injuries caused by UV radiation, consisting in maintaining on the skin during the irradiation an effective amount of a cosmetic composition comprising the abovementioned cupric complex of 3,5-diisopropylsalicylic acid.

Other subjects and characteristics of the invention will become apparent on reading the description which follows.

The cosmetic composition according to the invention contains, in a fatty phase, the cupric complex of 3,5-diisopropylsalicylic acid in a concentration range extending from 0.01 to 5%, and preferably from 0.05 to 1%, by weight based on the total weight of the composition. It should be noted that the above cupric complex, although coloured in solution, does not colour the skin at the concentrations used.

As a result of the fat-soluble nature of the cupric complex used, the cosmetic compositions according to the invention contain at least one fatty phase. They can take the form of oils, oleo-alcoholic lotions, emulsions such as creams or milks, fatty or oleo-alcoholic gels, or solid sticks, or can be packaged as an aerosol.

The fatty phase consists of fats such as mineral, animal or vegetable oils or waxes, fatty acids, fatty acid triglycerides having from 6 to 18 carbon atoms and fatty alcohols.

In addition to the fatty phase, the cosmetic vehicle can also contain lower monohydric alcohols or polyhydric alcohols containing from 1 to 6 carbon atoms, or alternatively water and mixtures of these different constituents.

The mono- or polyhydric alcohols which are more especially preferred are chosen from ethanol, isopropanol, propylene glycol, glycerol and sorbitol. The aqueous-alcoholic mixtures are preferably mixtures of water and ethanol.

By way of fats, the following may be used:

mineral oils such as liquid paraffin;

animal oils such as whale, seal, menhaden, halibut-liver, cod, tuna, tortoise, tallow, neat's-foot, horse's-foot, sheep's-foot, mink, otter and marmot oils;

vegetable oils such as almond, groundnut, wheat-germ olive, maize-germ, jojoba, sesame, sunflower, palm, walnut and rapeseed oils.

It is also possible to use the following as fats: vaseline, paraffin, hydrogenated lanolin, acetylated lanolin and silicone oils.

As waxes, it is possible to use sipol wax, lanolin wax, beeswax, candelilla wax, microcrystalline wax, carnauba wax, spermaceti, cocoa butter, shea butter, silicone waxes, hydrogenated oils which are solid at 25° C., sucroglycerides, and Ca, Mg, Zn and Al oleates, myristates, linoleates and stearates.

Among fatty alcohols, lauryl, cetyl, myrystyl, stearyl, palmityl and oleyl alcohols may be mentioned.

The cosmetic composition according to the invention can also contain nonionic, anionic, cationic or amphoteric emulsifiers.

It can also be advantageous to use thickeners such as cellulose derivatives, polyacrylic acid derivatives, guar or carob gums or xanthan gums.

The cosmetic composition according to the invention can also contain adjuvants customarily used in cosmetics and in particular moisturizing products, emollients, preservatives, dyestuffs, opacifiers, perfumes and propellants; the propellants are traditional propellants such as alkanes, fluoroalkanes and chlorofluoroalkanes.

The cosmetic composition according to the invention possesses a pH of between 4 and 9, and preferably between 5.5 and 8, which can optionally be adjusted using a pH-regulating agent.

The cosmetic composition according to the invention can also contain, in combination with the cupric complex of 3,5-diisopropylsalicylic acid, at least one sunscreen which absorbs radiation of wavelengths between 280 and 400 nm.

The total concentration of sunscreen(s) is between 0.5 and 20% of the total weight of the composition.

These sunscreens are chosen from derivatives of:

p-aminobenzoic acid;

cinnamic acid;

benzylidenecamphor;

salicylic acid;

anthranilic acid;

urocanic acid;

benzophenone;

dibenzoylmethane;

benzotriazole;

benzimidazolesulphonic acid.

They are chosen, in particular, from those mentioned in the article: "UV absorbers in sun cosmetics 1978", D.H. LIEM and L.T.H. HILlDERINK, International Journal of Cosmetic Science 1, 341–361 (1979).

It is also possible to use screening polymers such as those described in the Applicant's French Patents 2,237,912 and 2,359,857.

One embodiment of the invention is an emulsion in the form of a cream or milk comprising, in addition to the cupric complex, fatty alcohols, fatty acid esters and, in particular, fatty acid triglycerides, fatty acids, lanolin, natural or synthetic oils or waxes, and emulsifiers, in the presence of water.

Another embodiment of the cosmetic composition of the invention consists of oils based on natural or synthetic oils and waxes, lanolin and fatty acid esters, in particular fatty acid triglycerides, or of oleo-alcoholic lotions based on oils, waxes, fatty acid esters such as fatty acid triglycerides and lower alcohols such as ethanol or glycols such as propylene glycol or polyols such as glycerol.

The cosmetic composition of the invention can also be a fatty gel comprising oils or waxes and a thickener such as silica; the oleo-alcoholic gels comprise, in addition one or more lower alcohols or polyols such as ethanol, propylene glycol or glycerol.

The solid sticks consist of natural or synthetic waxes and oils, fatty alcohols, fatty acid esters, lanolin and other fats.

The examples which follow are designed to illustrate the invention without, however, being limiting in nature.

EXAMPLE 1

The following ingredients are mixed, heating if desired to 40–45° C. in order to homogenize:

| | |
|---|---|
| Cu (II) bis(3,5-diisopropylsalicylate) | 1 g |
| Perfume qs | |
| Rapeseed oil qs | 100 g |

EXAMPLE 2

| Skin protection cream | |
|---|---|
| Cu (II) bis(3,5-diisopropylsalicylate) | 0.5 g |
| Mixture of cetyl/stearyl alcohol (80%) and cetyl/stearyl alcohol oxyethylenated with 33 moles of ethylene oxide (20%) | 7 g |
| Non-self-emulsifying glycerol mono- and distearate | 2 g |
| Cetyl alcohol | 1.5 g |
| Liquid paraffin | 15 g |
| Glycerol | 10 g |
| Sorbitol | 5 g |
| Perfume, preservative qs | |
| Water qs | 100 g |

This cream is prepared according to the conventional techniques for preparing emulsions, by dissolving the cupric complex in the fats and the emulsifiers, heating this fatty phase to about 75–80 ° C. and adding, with vigorous stirring, the water, glycerol and sorbitol, also heated to 75–80° C. Stirring is maintained for 10 to 15 minutes, the mixture is then left to cool with moderate stirring and to about 40° C., and perfume and preservative are added.

EXAMPLE 3

| Skin protection cream | |
|---|---|
| Cetyl/stearyl alcohol oxyethylenated with 15 moles of ethylene oxide | 3 g |
| Mixture of non-self-emulsifying glycerol mono- and distearates | 4.8 g |
| Myristyl alcohol | 4.5 g |
| Liquid paraffin | 18 g |
| Cu (II) bis(3,5-diisopropylsalicylate) | 0.5 g |
| 2-Ethylhexyl p-(dimethylamino)benzoate, VAN DYK "ESCALOL 507" | 2.75 g |
| 3-Benzylidene-DL-camphor | 2 g |
| Propylene glycol | 6 g |
| Preservative, perfume qs | |
| Water qs | 100 g |

This cream is prepared in the same manner as in Example 2.

EXAMPLE 4

| Skin protection oil | |
|---|---|
| Cu (II) bis(3,5-diisopropylsalicylate) | 0.2 g |
| Octyl p-methoxycinnamate sold by the company GIVAUDAN under the name "PARSOL MCX" | 5 g |
| Liquid paraffin | 40 g |
| Preservative, perfume qs | |
| Benzoate of $C_{12}$–$C_{15\ primary\ alcohols}$, sold by the company FINETEX under the name "FINSOLV TN" qs | 100 g |

This oil is prepared in the same manner as in Example 1.

What is claimed is:

1. Cosmetic composition for protecting the skin against ultraviolet radiation of wavelengths between 280 and 400 nm, which consists essentially of 0.01 to 5% by weight of copper (II) bis(3,5-diisopropylsalicylate) of formula:

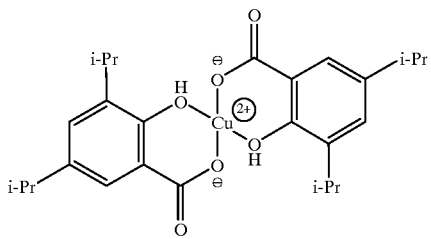

and a cosmetic vehicle containing at least one fatty phase and at least one cosmetic adjuvant selected from the group consisting of nonionic, anionic, cationic and amphoteric emulsifiers, thickeners, moisturizing products, emollients, preservatives, colourings, opacifiers, pH-regulating agents, propellants and perfumes.

2. Cosmetic composition for protecting the skin against ultraviolet radiation of wavelengths between 280 and 400 nm, which comprises, in a cosmetic vehicle containing at least one fatty phase, an effective amount of copper (II) bis(3,5-diisopropylsalicylate) of formula:

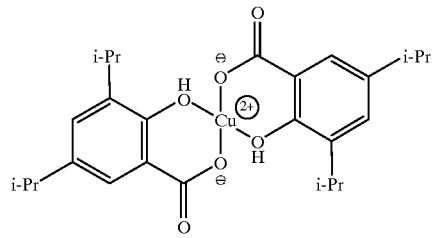

which contains, in addition, one or more sunscreens which absorb ultraviolet radiation in the wavelength range extending from 280 to 400 nm.

3. Cosmetic composition according to claim 2, wherein the sunscreens are present in proportions of between 0.5 and 20% by weight based on the total weight of the composition.

4. Cosmetic composition according to claim 2, wherein the sunscreens are selected from the group consisting of derivatives of p-aminobenzoic acid, of cinnamic acid, of benzylidenecamphor, of salicylic acid, of anthranilic acid, of urocanic acid, of benzophenone, of dibenzoylmethane, of benzotriazole and of benzimidazolesulphonic acid.

5. Cosmetic composition according to claim 1, in the form of an oil, an oleo-alcoholic lotion, an emulsion, a fatty or oleo-alcoholic gel, a solid stick or an aerosol.

6. Cosmetic composition according to claim 1, wherein the fatty phase comprises mineral, animal and vegetable oils or waxes, fatty acids, fatty acid triglycerides having from 6 to 18 carbon atoms and fatty alcohols.

7. Cosmetic composition according to claim 1, wherein the cosmetic vehicle further contains lower monohydric or polyhydric alcohols containing from 1 to 6 carbon atoms, water or mixtures of these compounds.

8. Process for protecting the human epidermis against injuries caused by ultraviolet radiation, which consists in maintaining on the skin during the irradiation an effective amount of a cosmetic composition according to claim 4.

9. Cosmetic composition according to claim 1, which contains 0.05 to 1% by weight of copper (II) bis(3,5-diisopropylsalicylate).

10. Cosmetic composition according to claim 5, wherein the emulsion is a cream or a milk.

* * * * *